(12) United States Patent
Dimoulis

(10) Patent No.: US 6,364,158 B1
(45) Date of Patent: Apr. 2, 2002

(54) ANESTHETIC DISPENSING STATION AND METHOD OF USING SAME

(76) Inventor: John Dimoulis, 2805 Briarwood Dr. West, Arlington Heights, IL (US) 60005

(*) Notice: Subject to any disclaimer, the term of this patent is extended or adjusted under 35 U.S.C. 154(b) by 0 days.

(21) Appl. No.: 09/534,722

(22) Filed: Mar. 24, 2000

(51) Int. Cl.[7] .............................................. B65H 5/00
(52) U.S. Cl. ..................................... 221/238; 221/270
(58) Field of Search ............................. 221/150 A, 135, 221/194, 195, 196, 232, 191, 238, 236, 268, 270, 271, 276, 255, 256, 257

(56) References Cited

U.S. PATENT DOCUMENTS

| | | | | |
|---|---|---|---|---|
| 2,784,873 A | * | 3/1957 | Hartnett | 221/238 |
| 3,162,322 A | | 12/1964 | Gilbertson | 221/135 |
| 4,526,292 A | | 7/1985 | Waxman | 221/97 |
| 5,482,183 A | * | 1/1996 | Beal et al. | 221/256 |

OTHER PUBLICATIONS

Sullivan–Schein, Dental Catalog showing "Cartridge Dispenser & Warmer Premier", 2000, p. 40.

* cited by examiner

Primary Examiner—Kenneth W. Noland
(74) Attorney, Agent, or Firm—Sheridan Ross P.C.

(57) ABSTRACT

A dispensing station for individually dispensing tubular members is disclosed herein. The dispensing station includes a housing having an aperture therein. Tubular members are stored within the housing and an actuator protrudes from the housing. When a force is exerted on the actuator in a first direction, a tubular member is dispensed through the aperture in the housing in a second direction, wherein the second direction is perpendicular to the first direction. The actuator protrudes from the housing such that the actuator may be depressed without a user's hands. For example, the actuator may be depressed using one's forearm or elbow. Furthermore, the tubular member is dispensed through the aperture such that the user may manually retrieve the tubular member without contacting the housing. Advantageously, the tubular member may be dispensed without contaminating the dispenser. A method for individually dispensing tubular members is also disclosed herein.

27 Claims, 3 Drawing Sheets

US 6,364,158 B1

ANESTHETIC DISPENSING STATION AND METHOD OF USING SAME

FIELD OF THE INVENTION

The present invention is directed to an anesthetic dispensing station and method of using same, and more particularly, to an anesthetic dispensing station which may be operated to individually dispense hypodermic needles and/or liquid anesthetic cartridges.

BACKGROUND OF THE INVENTION

In the practice of medicine, particularly dentistry, a clinician or dentist will regularly use a number of medical tools and materials to administer local anesthetic to a patient. These medical tools and materials include hypodermic syringes and needles, cotton-tipped swabs, gauze, topical anesthetic gel, and cartridges containing liquid anesthetics such as novocaine, lidocaine, epinephrine or isocaine. The dentist will use gauze to wipe saliva from the area to be anesthetized and then apply topical anesthetic gel to the area using a cotton-tipped swab. The dentist will then administer the liquid anesthetic to the area using a hypodermic syringe and needle.

In administering local anesthetic, it would be convenient and efficient for the dentist to have all of the necessary medical tools and materials collected and dispensed from a single location or station. This would be helpful not only to save precious space and facilitate organization of today's compact dental offices, but also would allow the dentist to easily retrieve additional medical tools and materials for administering further local anesthetic should it be required during a procedure.

A number of devices have been developed for holding and dispensing some of the necessary medical tools and materials for administering local anesthetic. For example, U.S. Pat. No. 3,162,322 to Gilbertson discloses a dispenser for holding a plurality of liquid anesthetic cartridges for individual dispensing. The Gilbertson device is operated by manually squeezing two side handles together, causing a cartridge to drop into a slot cavity where a piston then pushes the cartridge laterally forward into the open end of the slot to be retrieved by the user. Importantly, the device disclosed in Gilbertson does not provide containers to hold the other medical tools and materials which are used in dental procedures in conjunction with the cartridges held in the device. In addition, in operation of the Gilbertson device, the user must necessarily use his or her hands, thereby contaminating the device with blood and/or saliva if handled during a medical procedure. Not only must the user operate the handles with contaminated hands, but retrieval of the laterally oriented cartridge increases the chance that the user will also contact the area surrounding the open end of the slot.

Another device for holding and dispensing some of the necessary medical tools and materials for administering local anesthetic is disclosed in U.S. Pat. No. 4,546,292 to Waxman. Waxman discloses a chest for storing, heating and dispensing hypodermic needles and liquid anesthetic cartridges. The chest also includes a number of openings for holding hypodermic syringes. The user operates the Waxman device by depressing a handle which causes an individual cartridge or hypodermic needle to roll from an inclined ramp into a slot in the handle and then into a retainer shelf when the handle is released. Subsequently, the cartridge may then be retrieved. Like the Gilbertson device, the configuration of the Waxman device necessarily requires the user to depress the handle with contaminated hands if the device is used during a medical procedure. Also, while including openings for holding hypodermic syringes, the Waxman device does not provide containers to hold the other medical tools and materials which are used in dental procedures in conjunction with the cartridges held in the device, such as topical anesthetic gel, cotton-tipped swabs and gauze.

It should be understood that the descriptions provided for the above-discussed patents are intended to be synopses of such patents. Reference should be made directly to the patents to completely understand the information disclosed therein.

SUMMARY OF THE INVENTION

The present invention is designed to overcome the aforementioned problems and meet the aforementioned, and other, needs.

The present invention is directed to a dispensing station for individually dispensing tubular members. In one embodiment, the dispensing station includes a housing having an aperture therein. Tubular members are stored within the housing and an actuator protrudes from the housing. When a force is exerted on the actuator in a first direction, a tubular member is dispensed through the aperture in the housing in a second direction, wherein the second direction is perpendicular to the first direction. The actuator protrudes from the housing such that the actuator may be depressed without a user's hands. For example, the actuator may be depressed using one's forearm or elbow. Furthermore, the tubular member is dispensed through the aperture such that the user may manually retrieve the tubular member without contacting the housing. Advantageously, the tubular member may be dispensed without contaminating the dispenser. A method for individually dispensing tubular members is also disclosed herein.

Other embodiments, objects, features and advantages of the invention will be apparent from the following specification taken in conjunction with the following drawings.

DETAILED DESCRIPTION OF THE PREFERRED EMBODIMENT

Figure 1:
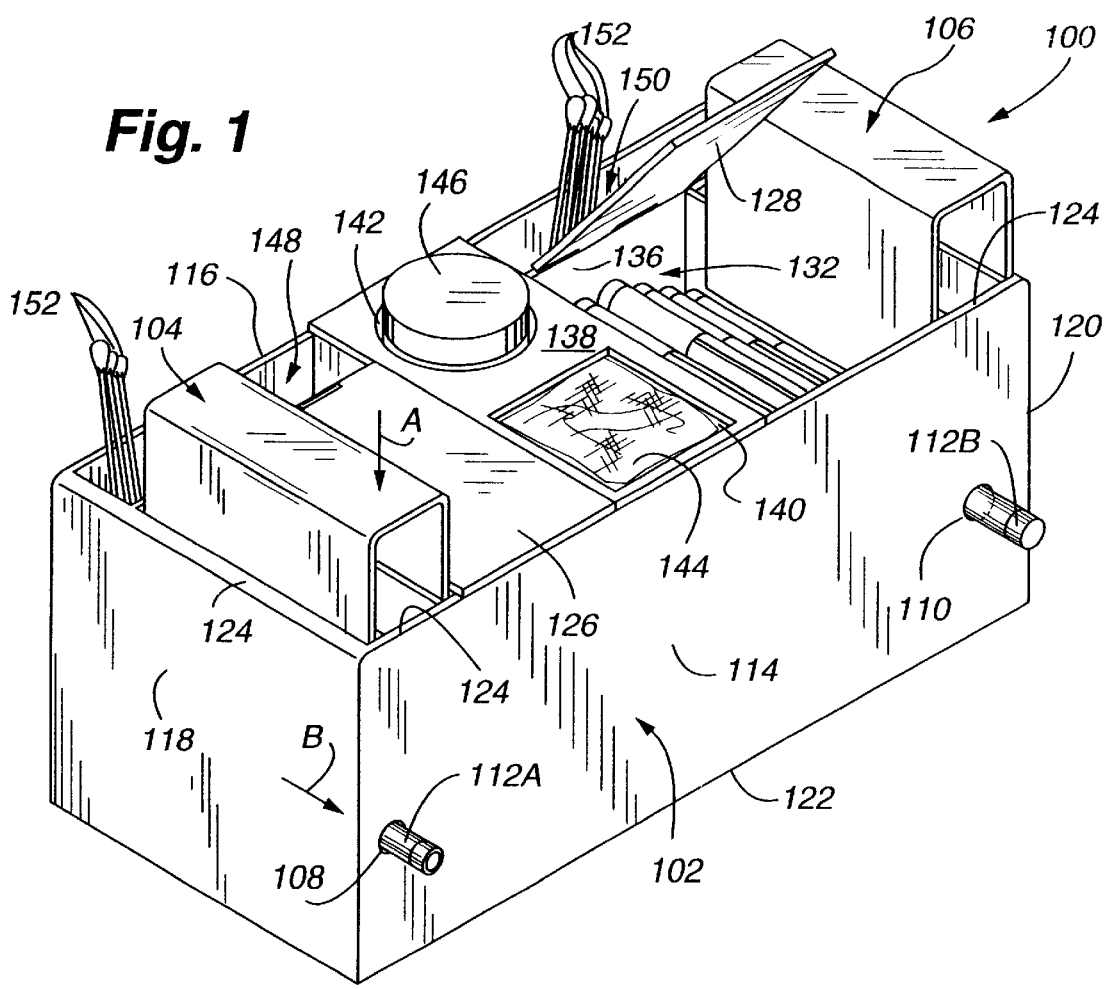
FIG. 1 is a perspective view of an anesthetic dispensing station in accordance with one embodiment of the present invention.

While this invention is susceptible of embodiments in many different forms, there is shown in the drawings and will herein be described in detail, preferred embodiments of the invention with the understanding that the present disclosure is to be considered as an exemplification of the principles of the invention and is not intended to limit the broad aspects of the invention to the embodiments illustrated.

A perspective view of one embodiment of an anesthetic dispensing station used for individually dispensing hypodermic needle cartridges and/or liquid anesthetic cartridges in accordance with the present invention is illustrated in FIG. 1 and is generally designated 100. The anesthetic dispensing station 100 shown in FIG. 1 includes a housing 102, a first actuator 104 and a second actuator 106, wherein the first actuator 104 and the second actuator 106 protrude from the housing 102. The housing 102 includes a first aperture 108 and a second aperture 110, through which tubular members 112A, 112B are respectively dispensed. The tubular members 112A are preferably are liquid anesthetic cartridges, while tubular members 112B are preferably hypodermic needle cartridges.

In operation, a first force is applied in a first direction (see direction of arrow A) on the first actuator 104 (e.g., causing the first actuator 104 to move downwardly). The first force is translated into a second force in a second direction (see direction of arrow B), wherein the direction of the first force and the direction of the second force are generally perpendicular to one another, which causes tubular member 112A to be dispensed from housing 102 through aperture 108. Similarly, when a first force is applied in a first direction (see direction of arrow A) on the second actuator 106 (e.g., causing the second actuator 106 to move downwardly), the first force is translated into a second force in a second direction (see direction of arrow B), wherein the direction of the first force is generally perpendicular to the direction of the second force. Thus, tubular member 112B is dispensed from housing 102 through aperture 110.

Advantageously, when a dentist (or other health care professional) has contaminated hands, the dentist may apply the first force in the first direction with their elbow or forearm (among other things) to avoid contamination of the first actuator 104 (or second actuator 106). In addition, the dentist can avoid contaminating the housing 102 because the tubular member 112A will protrude from the housing 102 (see FIG. 4C) once dispensed.

Referring again to FIG. 1, the housing 102 may include a front 114, a back 116, a first side 118, a second side 120, a bottom 122 and an upper lip 124. The bottom 122 of the housing 102 may have rubber feet affixed thereto to prevent inadvertent movement of the aesthetic dispensing station 100 during use. Alternatively, the anesthetic dispensing station 100 may be affixed to a surface to prevent unwanted movement by using suction cups, Velcro™, double-sided foam tape, screws or bolts, among other things. Alternatively, the back 116 of the housing 102 of the anesthetic dispensing station 100 could be affixed to a vertical surface using one or more of the above.

As shown in FIG. 1, preferably, the first aperture 108 and the second aperture 110 are in the front 114 of the housing 102. As will be appreciated by those skilled in the art, the size of the first and second apertures 108, 110 must be greater than the outside diameter of the tubular members 112A, 112B intended to be dispensed therefrom, but should be as small as possible to minimize entry of foreign material or objects into the anesthetic dispensing station 100. In addition, preferably, first actuator 104 and second actuator 106 protrude above (in the orientation shown in FIG. 1) upper lip 124.

The anesthetic dispensing station 100 may further include a first lid 126 and a second lid 128, which respectively allow access to first compartment 130 (not shown in FIG. 1) and second compartment 132. The first and second lids 126, 128 allow tubular members 112A, 112B to be loaded into or removed from first and second compartments 130, 132, respectively. The first lid 126 is preferably hingeably attached to first interior wall 134 (not shown in FIG. 1), while the second lid 128 is preferably hingeably attached to second interior wall 136.

The anesthetic dispensing station 100 may also include a panel 138 which preferably extends from the front 114 of the housing 102 to the back of the housing 116. The panel 138 preferably includes a first cut-out 140 and a second cut-out 142. The first cut-out 140 is sized to allow gauze 144 to be dispensed therefrom. The second cut-out 142 is sized to receive a jar of topical anesthetic gel 146. Finally, the anesthetic dispensing station 100 preferably also includes a first chamber 148 and a second chamber 150, both of which may be used to store cotton-tipped swabs 152 (among other things).

It should be understood that the embodiment shown in FIG. 1 is the preferred embodiment of the invention. In other embodiments, for example, the first chamber 148 and second chamber 150 (and hence the first and second interior walls 134, 136) could be removed. In such case, the first and second lids 126, 128 could be hingeably attached to the back 116 of the housing 102. In another embodiment, for example, the first and second lids 126, 128 could be hingeably attached to the front 114 of the housing 102. A further embodiment, for example, may include only one actuator instead of first and second actuators 104, 106. Yet another embodiment, for example, may not include panel 138.

Figure 2:
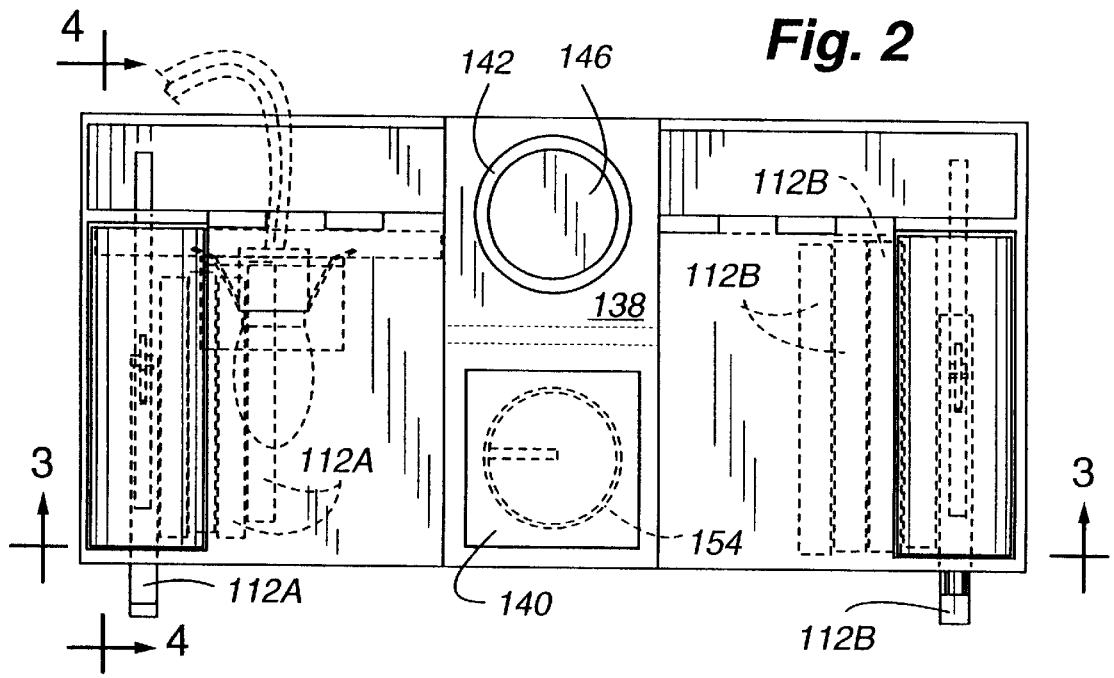
FIG. 2 is a top view, partially in phantom, of the anesthetic dispensing station shown in FIG. 1.
Figure 3:
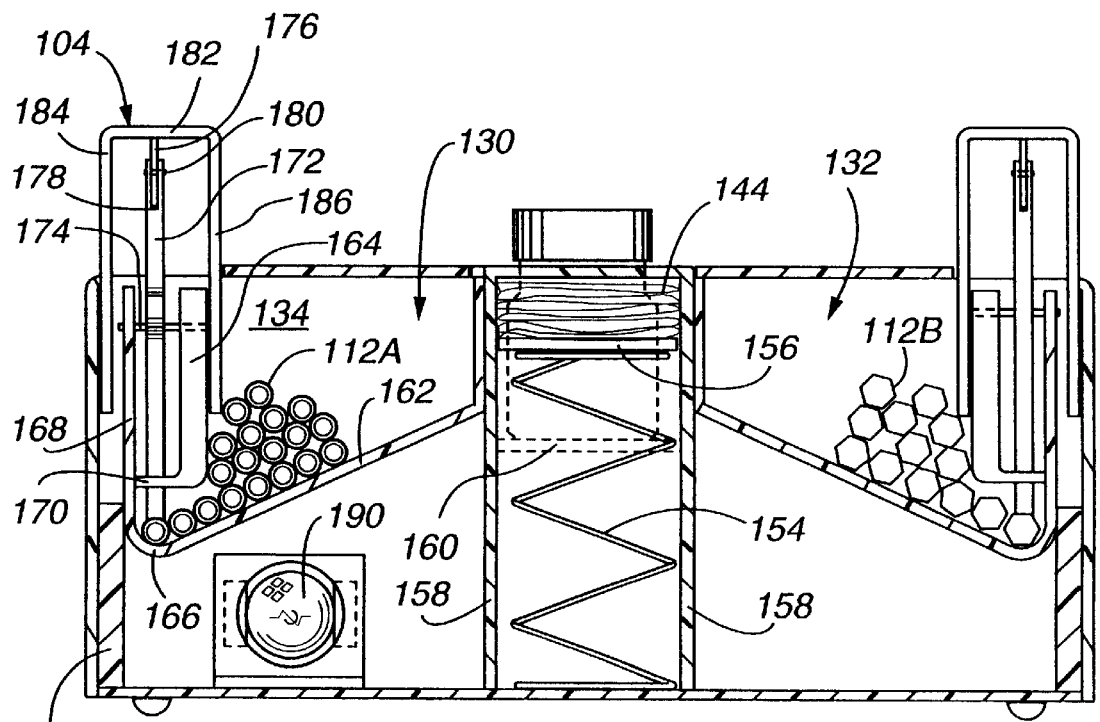
FIG. 3 is a sectional view taken along line 3—3 of FIG. 2.

FIG. 2 illustrates a top view, partially in phantom, of the anesthetic dispensing station 100 of FIG. 1, while FIG. 3 is a sectional view taken along line 3—3 of FIG. 2. Referring now to FIGS. 2 and 3, gauze 144 is dispensed via a gauze dispenser comprised of the first cut-out 140 in the panel 138, a spring 154, a floating support surface 156 and a guide tube 158. The guide tube 158 is preferably square or rectangular (but may take on any appropriate shape), and is sized to the dimensions of gauze pads 144 which are to be contained therein. The floating support surface 156 is moveable within guide tube 158, biased towards the first cut-out 140 via spring 154, and used to support a stack of gauze pads 144 thereon. Preferably, spring 154 is affixed to the interior side of the bottom 122 of the housing 102. As will be appreciated by those skilled in the art, the first cut-out 140 should have dimensions slightly smaller than the dimensions of the gauze pads 144 in order to retain the gauze pads 144 within the guide tube 158, while still permitting easy removal of the top gauze pad.

Still referring to FIGS. 2 and 3, the jar of topical anesthetic gel 146 is supported by an interior support surface 160 (see FIG. 3) for supporting and maintaining the jar of topical anesthetic gel 146 at an appropriate height above the second cut-out 142 in the panel 138 for easy access by a user.

Referring now to FIG. 3, a preferred mechanism for dispensing tubular members 112A (e.g., anesthetic cartridges) will be described. As will be understood by those skilled in the art and as is shown in the figures, the preferred mechanism for dispensing tubular members 12B (e.g., hypodermic needle cartridges) is similar to that for dispensing tubular members 112A. Accordingly, for brevity and clarity, only the mechanism for dispensing tubular members 112A will be described.

Compartment 130 includes a ramped surface 162 for guiding tubular members 112A, via gravitational forces, past singulating wall 164 towards a trough 166 at the lowermost portion of the ramp 162. The trough 166 is formed by the ramped surface 162 and upstanding member 168, which is preferably integral with ramped surface 162. As tubular members 112A are guided past singulating wall 164, they line up in a single file fashion, as shown in FIG. 3. Accordingly, the shortest distance between singulating wall 164 and ramped surface 162 is preferably greater than the diameter of one of the tubular members 112A but less than the diameter of two tubular members 112A. The singulating wall 164 preferably extends from the front 114 of the housing 102 to the first interior wall 134 (or back 116 in embodiments where there is no first interior wall 134).

In order to ensure that the tubular members 112A remain singulated after they are guided past singulating wall 164, a singulating lip 170 extends from singulating wall 164 towards upstanding member 168. Preferably, the singulating lip 170 is integral with singulating wall 164. It should be noted that singulating lip 170 may be angled towards trough 166 as it extends from singulating wall 164,to upstanding member 168.

A dispensing lever 172 is preferably disposed between singulating wall 164 and upstanding member 168, and pivots about first pivot pin 174 (which is preferably supported by singulating wall 164 and upstanding member 168). Dispensing lever 172 has a roller 176 rotatably mounted within a cutout 178 in the dispensing lever 172 by pintle 180. The roller 176 contacts the underside of first actuator 104.

More specifically, the actuator 104 includes a shoulder 182, a first arm 184 and a second arm 186. The roller 176 bears against the underside of shoulder 182.

A travel-limit wall 188 cooperates with first arm 184 of actuator 104 to limit travel of the actuator 104. The travel-limit wall 188 is designed to permit second arm 186 of actuator 104 to extend past singulating wall 164 for the purpose of agitating the tubular members 112A, so that the tubular members 112A are prevented from jamming between the singulating wall 164 and the ramped surface 162. In addition, travel-limit wall 188 is designed to prevent the second arm 186 of actuator 104 from contacting ramped surface 162.

The anesthetic dispensing station 100 may also be provided with a heating element 190 (shown as a lightbulb in FIG. 3) preferably located beneath first compartment 130 (wherein tubular members 112A are, for example, liquid anesthetic cartridges). To allow the heat generated by the heating element to warm tubular members 112A in the first w compartment 130, the ramped surface 162 may include apertures (not shown) therein.

Figure 4A:
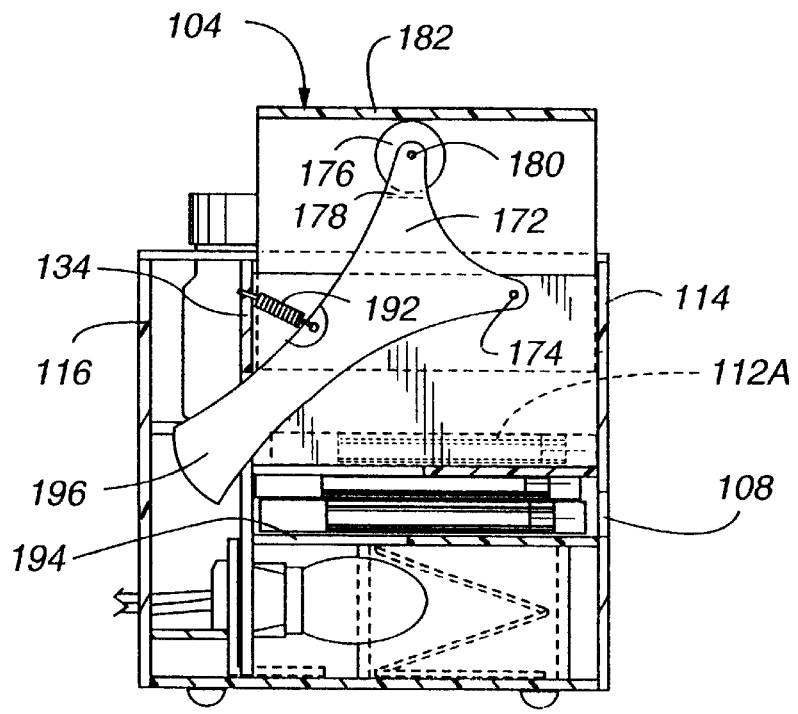
FIG. 4A is a sectional view taken along line 4—4 of FIG. 2, wherein the actuator has not yet been depressed.

Referring now to FIG. 4A, a biasing spring 192 is affixed to both the first interior wall 134 and the dispensing lever 172 to bias the dispensing lever 172 away from first aperture 108. In addition, FIG. 4A shows a slot 194 in trough 166. The slot 194 is large enough to allow dispensing lever 172 to travel therein when engaging a tubular member 112A, but small enough to prevent tubular members 112A from falling therethrough. The slot 194 also operates to limit the travel of the dispensing lever 172 and, accordingly, may be sized with reference to first arm 184, second arm 186 and travel-limit wall 188 (among other things).

Figure 4B:
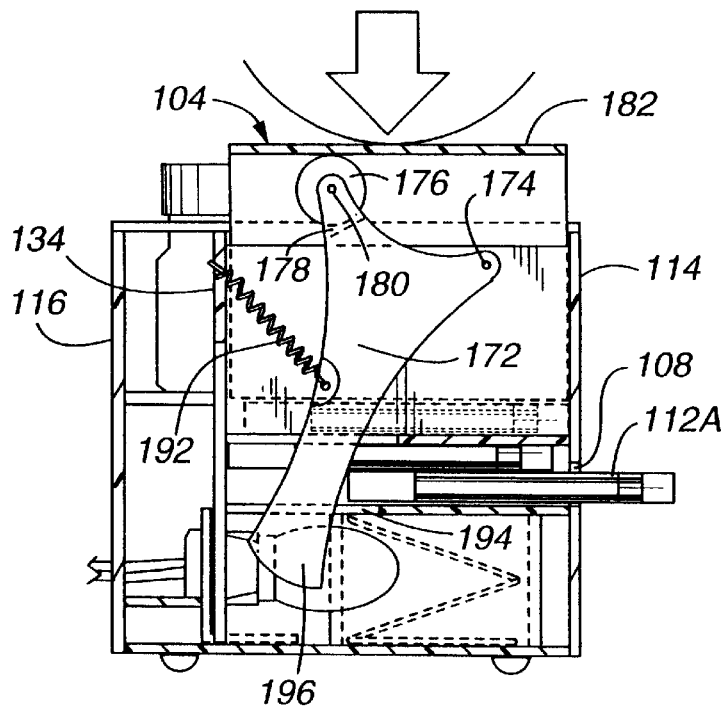
FIG. 4B is a sectional view similar to FIG. 4A, wherein the actuator is in a partially depressed position.
Figure 4C:
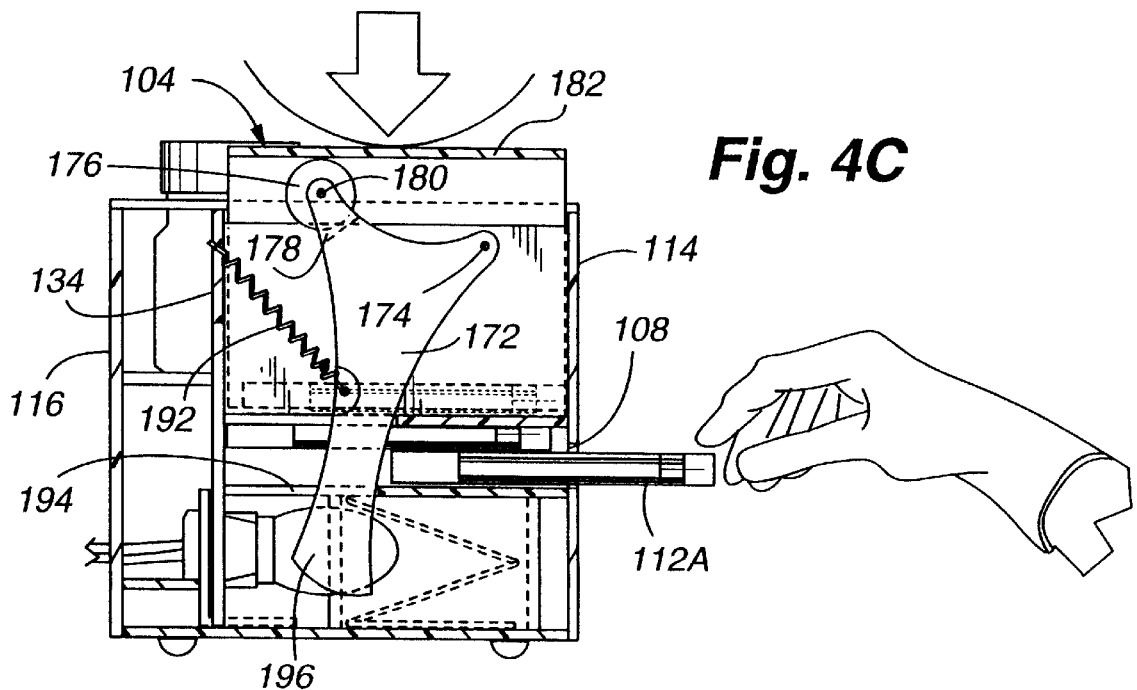
FIG. 4C is a sectional view similar to FIG. 4A, wherein the actuator is in a depressed position.

FIGS. 4A, 4B and 4C (in combination with FIGS. 1, 2 and 3) will be used to describe the operation of the anesthetic dispensing station 100. The description will be directed to the first actuator 104 and the first compartment 130, with the understanding that the second actuator 106 and second compartment 132 function similarly. FIG. 4A illustrates first actuator 104 prior to being depressed; FIG. 4B illustrates the first actuator 104 in a partially-depressed position; and, FIG. 4C illustrates the first actuator 104 in a depressed position.

In operation, first and second compartments 130,132 are filled with tubular members (e.g., liquid anesthetic cartridges 112A, hypodermic needle cartridges 112B or other tubular members). The slope of the ramped surface 162 of the first compartment 130 forces the tubular members 112A to collect against the singulating wall 164 and causes a tubular member 112A to be positioned in trough 166 (see FIG. 3).

When desiring to dispense a tubular member 112A from the anesthetic dispensing station 100, a user depresses the first actuator 104 by applying a downward force (see direction of force A in FIG. 1). When the first actuator 104 is depressed, the roller 176 engages shoulder 182 causing dispensing lever 172 to rotate about first pivot pin 174 (see FIGS. 3, 4A, 4B and 4C). More specifically, the roller 176 moves towards the back 116 of the housing 102, while lower portion 196 of dispensing lever 172 moves towards the front 114 of the housing 102. The dispensing lever 172 (more specifically, its lower portion 196) engages the tubular member 112A resting in the trough 166. The tubular member 112A is pushed towards the front 114 of the housing 102 and through the first aperture 108.

In the preferred embodiment of the present invention, the tubular member 112A is pushed forward such that it extends through the first aperture 108 and protrudes beyond the front 114 of the housing 102 by a distance sufficient to permit the user to easily grasp the tubular member 112A with his or her hand without grazing the housing 102 (see FIG. 4C), but not so far that the tubular member 112A will fall out of the first aperture 108 under its own weight.

Concurrent with the dispensing of a tubular member 112A, the second arm 186 is forced into a stack of tubular members 112A (see FIG. 3) remaining in the first compartment 130. The second arm 186 is used to agitate the stack to prevent jamming of tubular members 112A between the singulating wall 164 and the ramped surface 162. As will be appreciated by those skilled in the art, there are numerous ways in which the stack of tubular members 112A may be mechanically agitated other than by the method shown in the preferred embodiment.

The location of the first actuator 104, in the preferred embodiment of the present invention, allows the first actuator 104 to be easily depressed with either the user's forearm or elbow. Accordingly, the user whose hands may be covered in blood and/or saliva (or some other contaminant), may retrieve hypodermic needle cartridges and anesthetic cartridges from the anesthetic dispensing station 100 without contaminating the station with the blood and/or saliva. By providing a first dispensing actuator 104 which is unobstructed by any extraneous structure and which is depressable in a substantially vertical direction, the anesthetic dispensing station 100 can be easily operated to dispense necessary medical tools and materials without touching any component thereof with contaminated hands.

While an effort has been made to describe some alternatives to the preferred embodiment, other alternatives will readily come to mind to those skilled in the art. Therefore, it should be understood that the invention may be embodied in other specific forms without departing from the spirit or central characteristics thereof. The present examples and embodiments, therefore, are to be considered in all respects as illustrative and not restrictive, and the invention is not intended to be limited to the details given herein.

For example, the preferred embodiment may be modified to allow the first actuator 104 and the second actuator 106 to be removed, so that they can be sterilized after each patient.

In such case, the handles would be made of well-known materials that may be sterilized using known techniques (e.g., metal materials that are subjected to high temperatures). Since the first and second actuators 104, 106 would be sterilized after each patient, the clinician could use his hands to exert the force required to dispense a tubular member.

In another embodiment, the dispenser may permit the tubular members to be completely ejected from housing onto a tabletop. A padded surface having a large gauze pad (or some other fungible material) may be placed on the tabletop to cushion the landing of the tubular member.

Furthermore, as will be appreciated by those skilled in the art, the anesthetic dispensing station 100 could be modified to dispense tubular members through use of an electromechanical device, including, but not limited to, a solenoid, a motorized rotating wheel, or one or both of the foregoing. These electromechanical devices could be combined with other basic mechanical components to push the tubular member 112A resting in the trough 166 in a longitudinal direction through the first aperture 108. In addition, an electric or electronic device may be used to initiate operation of the electromechanical device, including, but not limited to, a photo-eye or some other proximity-sensing device for sensing the presence of the user's hand positioned to retrieve a dispensed tubular member. Further, an electric switch affixed either to the housing 102 or remotely, such as a foot activated switch, may be used to initiate operation of the electromechanical device.

What is claimed is:

1. A dispensing station for individually dispensing tubular members comprising:
    a housing having an aperture therein, said tubular members being stored within said housing;
    an actuator protruding from said housing, wherein a force exerted on the actuator in a first direction causes a tubular member to dispensed through the aperture in the housing in a second direction, the second direction being perpendicular to the first direction, and
        wherein the actuator protrudes from the housing such that the actuator may be depressed without a user's hands and wherein the tubular member is dispensed through said aperture such that the user may manually retrieve the tubular member without contacting the housing.

2. The dispensing station of claim 1 wherein the tubular member is dispensed from the dispenser in a substantially longitudinal direction relative to said tubular member.

3. The dispensing station of claim 1 wherein the tubular member is an anesthetic cartridge and wherein the dispensing station farther includes means for dispensing gauze and means for storing a topical anesthetic container.

4. A dispensing station for individually dispensing tubular members comprising:
    a housing having an aperture therein, said tubular members being stored within said housing;
    an actuator protruding from said housing, wherein a force exerted on the actuator in a first direction causes a tubular member to dispensed through the aperture in the housing in a second direction, the second direction being perpendicular to the first direction;
    a ramped surface, located inside the housing, used to guide said tubular members toward said aperture; and,
    a dispensing lever, located inside the housing, used to push the tubular member through the aperture, wherein the dispensing lever has a roller attached thereto and wherein the roller moves in a direction opposite to that of tubular member when said tubular member is being dispensed from said housing.

5. The dispensing station of claim 4 wherein the actuator includes an arm for agitating at least one tubular member, while another tubular member is being dispensed.

6. The dispensing station of claim 4 further including a singulating wall used to singulate tubular members as they move down the ramped surface towards the aperture.

7. A dispensing station for individually dispensing tubular members comprising:
    a housing having an aperture therein, said tubular members being stored within said housing; and,
    an actuator protruding from said housing, wherein a force exerted on the actuator in a first direction causes a tubular member to dispensed through the aperture in the housing in a second direction, the second direction being perpendicular to the first direction and wherein the actuator includes an arm for agitating at least one tubular member, while another tubular member is being dispensed.

8. The dispensing station of claim 7 wherein the tubular member is dispensed from the dispenser in a substantially longitudinal direction relative to said tubular member.

9. A dispensing station for individually dispensing tubular members comprising:
    a housing having an aperture therein, said tubular members being stored within said housing;
    an actuator protruding from said housing, wherein a force exerted on the actuator in a first direction causes a tubular member to dispensed through the aperture in the housing in a second direction, the second direction being perpendicular to the first direction;
    a ramped surface, located inside the housing, used to guide said tubular members toward said aperture; and,
    a singulating wall used to singulate tubular members as they move down the ramped surface towards the aperture.

10. The dispensing station of claim 9 wherein the tubular member is an anesthetic cartridge and wherein the dispensing station further includes means for dispensing gauze and means for storing a topical anesthetic container.

11. A method of individually dispensing tubular members comprising the steps of:
    providing a housing having an aperture, said tubular members being stored within said housing;
    providing an actuator which protrudes from said housing; and,
    exerting a force in a first direction upon said actuator causing a tubular member to be dispensed in a second direction, said second direction being perpendicular to said first direction, wherein the force is exerted using something other than a user's hands.

12. The method of claim 11 further including the step of:
    manually retrieving said tubular member, once it has been dispensed through said aperture, without contacting the housing.

13. The method of claim 12 wherein a ramped surface, located inside the housing, is used to guide said tubular members toward said aperture.

14. The method of claim 13 wherein a dispensing lever, located inside the housing, is used to push the tubular member through the aperture.

15. The method of claim 14 wherein the dispensing lever is pivoted about a pivot pin.

16. The method claim 14 wherein the dispensing lever has a roller attached thereto, wherein the roller moves in a direction opposite to that of tubular member when said tubular member is being dispensed from said housing.

17. The method of claim 14 wherein the actuator includes an arm for agitating at least one tubular member, while another tubular member is being dispensed.

18. The method of claim 14 further including a trough located at a bottom of said ramped surface, said trough being aligned with said aperture.

19. The method of claim 14 further including a singulating wall used to singulate tubular members as they move down the ramped surface towards the aperture.

20. The method of claim 14 further including a biasing spring, located inside said housing, for biasing said dispensing lever away from said aperture.

21. The method of claim 11 wherein the tubular member is dispensed from the dispenser in a substantially longitudinal direction relative to said tubular member.

22. The method of claim 12 wherein the tubular member is an anesthetic cartridge and wherein the dispensing station further includes means for dispensing gauze and means for storing a topical anesthetic container.

23. The method of claim 13 further comprising a heating element for warming the tubular members.

24. A method of individually dispensing tubular members comprising the steps of:
   providing a housing having an aperture, said tubular members being stored within said housing;
   providing an actuator which protrudes from said housing;
   exerting a force in a first direction upon said actuator causing a tubular member to be dispensed in a second direction, said second direction being perpendicular to said first direction; and,
   providing a dispensing lever, located inside the housing, used to push the tubular member through the aperture, wherein the dispensing lever has a roller attached thereto and wherein the roller moves in a direction opposite to that of tubular member when said tubular member is being dispensed from said housing.

25. A method of individually dispensing tubular members comprising the steps of:
   providing a housing having an aperture, said tubular members being stored within said housing;
   providing an actuator which protrudes from said housing; and,
   exerting a force in a first direction upon said actuator causing a tubular member to be dispensed in a second direction, said second direction being perpendicular to said first direction,
      wherein the actuator includes an arm for agitating at least one other tubular member, while another tubular member is being dispensed.

26. A method of individually dispensing tubular members comprising the steps of:
   providing a housing having an aperture, said tubular members being stored within said housing;
   providing an actuator which protrudes from said housing;
   exerting a force in a first direction upon said actuator causing a tubular member to be dispensed in a second direction, said second direction being perpendicular to said first direction;
   providing a ramped surface, located inside the housing, is used to guide said tubular members toward said aperture; and,
   providing a singulating wall used to singulate tubular members as they move down the ramped surface towards the aperture.

27. A method of individually dispensing tubular members comprising the steps of:
   providing a housing having an aperture, said tubular members being stored within said housing;
   providing an actuator which protrudes from said housing;
   exerting a force in a first direction upon said actuator causing a tubular member to be dispensed in a second direction, said second direction being perpendicular to said first direction,
      wherein the tubular member is an anesthetic cartridge and wherein the dispensing station further includes means for dispensing gauze and means for storing a topical anesthetic container.

* * * * *